(12) United States Patent
Chang

(10) Patent No.: US 8,069,855 B2
(45) Date of Patent: Dec. 6, 2011

(54) RESPIRATORY MASK

(75) Inventor: Eric Chang, Taichung Hsien (TW)

(73) Assignee: Hsiner Co., Ltd., Taichung Hsien (TW)

( * ) Notice: Subject to any disclaimer, the term of this patent is extended or adjusted under 35 U.S.C. 154(b) by 775 days.

(21) Appl. No.: 12/196,969

(22) Filed: Aug. 22, 2008

(65) Prior Publication Data
US 2009/0223523 A1 Sep. 10, 2009

(30) Foreign Application Priority Data

Mar. 10, 2008 (TW) ................................ 97108305 A

(51) Int. Cl.
*A62B 18/08* (2006.01)
*A62B 9/04* (2006.01)
*A62B 18/02* (2006.01)

(52) U.S. Cl. ......... 128/207.11; 128/202.27; 128/206.12; 128/206.16; 128/206.27; 128/206.28

(58) Field of Classification Search ............. 128/200.24, 128/202.27, 205.25, 206.21–207.13, 857, 128/863; D24/110, 110.4–110.5; *A62B 9/04, A62B 18/02, 18/08*
See application file for complete search history.

(56) References Cited

U.S. PATENT DOCUMENTS

| | | | | |
|---|---|---|---|---|
| 4,807,617 A * | 2/1989 | Nesti | | 128/205.12 |
| 6,968,844 B2 * | 11/2005 | Liland et al. | | 128/206.16 |
| 7,000,614 B2 | 2/2006 | Lang et al. | | |
| 7,021,311 B2 | 4/2006 | Gunaratnam et al. | | |
| 7,762,258 B2 * | 7/2010 | Zollinger et al. | | 128/206.24 |
| 7,861,715 B2 * | 1/2011 | Jones et al. | | 128/204.21 |
| 2002/0153012 A1 | 10/2002 | Gunaratnam et al. | | |
| 2010/0108072 A1 * | 5/2010 | D'Souza et al. | | 128/206.24 |
| 2010/0319700 A1 * | 12/2010 | Ng et al. | | 128/206.28 |
| 2011/0108036 A1 * | 5/2011 | Thomas | | 128/206.22 |

FOREIGN PATENT DOCUMENTS

| | | |
|---|---|---|
| CN | 1589920 A | 3/2005 |
| EP | 1475118 | 11/2004 |
| WO | WO 2007/041751 A | 4/2007 |

* cited by examiner

*Primary Examiner* — Loan Thanh
*Assistant Examiner* — Oren Ginsberg
(74) *Attorney, Agent, or Firm* — Fox Rothschild, LLP; Robert J. Sacco

(57) ABSTRACT

A respiratory mask includes: a rigid mask frame having a ring portion, a loop portion spaced apart from the ring portion, and rib portions interconnecting the ring portion and the loop portion, the rigid mask frame defining a frame space; and a single piece of a flexible mask body having a flat central portion, a surrounding portion extending outwardly and curvedly from the flat central portion, and a peripheral end portion flaring from the surrounding portion. The flat central portion is formed with an annular flange sleeved on the ring portion. The peripheral end portion is disposed outwardly of the frame space. The surrounding portion extends into the frame space and is restrained by the rib portions and the loop portion of the mask frame.

7 Claims, 7 Drawing Sheets

RESPIRATORY MASK

CROSS-REFERENCE TO RELATED APPLICATION

This application claims priority of Taiwanese application no. 097108305, filed on Mar. 10, 2008.

BACKGROUND OF THE INVENTION

1. Field of the Invention

The invention relates to a respiratory mask, more particularly to a respiratory mask including a mask body detachably framed by a mask frame.

2. Description of the Related Art

Referring to FIGS. 1 and 2, U.S. Pat. No. 7,021,311 discloses a respiratory mask 1 that includes a rigid mask frame 11 having a first rim portion 112, and a cushion 12 having a second rim portion 121 coupled detachably to the first rim portion 112 through a loop-shaped clip 13. The cushion 12 is used to contact the user's face.

The conventional respiratory mask 1 is disadvantageous in that since the connection between the mask frame 11 and the cushion 12 is through the first and second rim portions 112, 121, the size of the cushion 12 is required to be dependent on that of the mask frame 11. As such, only one size of the cushion 12 can be used for each size of the mask frame 11.

SUMMARY OF THE INVENTION

Therefore, an object of the present invention is to provide a respiratory mask that can overcome the aforesaid drawback associated with the prior art.

Accordingly, a respiratory mask of the present invention comprises: a rigid mask frame having a ring portion, a loop portion spaced apart from the ring portion, and rib portions interconnecting the ring portion and the loop portion, the rigid mask frame defining a frame space; and a single piece of a flexible mask body having a flat central portion, a surrounding portion extending outwardly and curvedly from the flat central portion, and a peripheral end portion flaring from the surrounding portion. The flat central portion of the mask body is formed with an annular flange protruding therefrom and sleeved on the ring portion of the mask frame. The peripheral end portion of the mask body is disposed outwardly of the frame space. The surrounding portion of the mask body extends into the frame space and is restrained by the rib portions and the loop portion of the mask frame.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
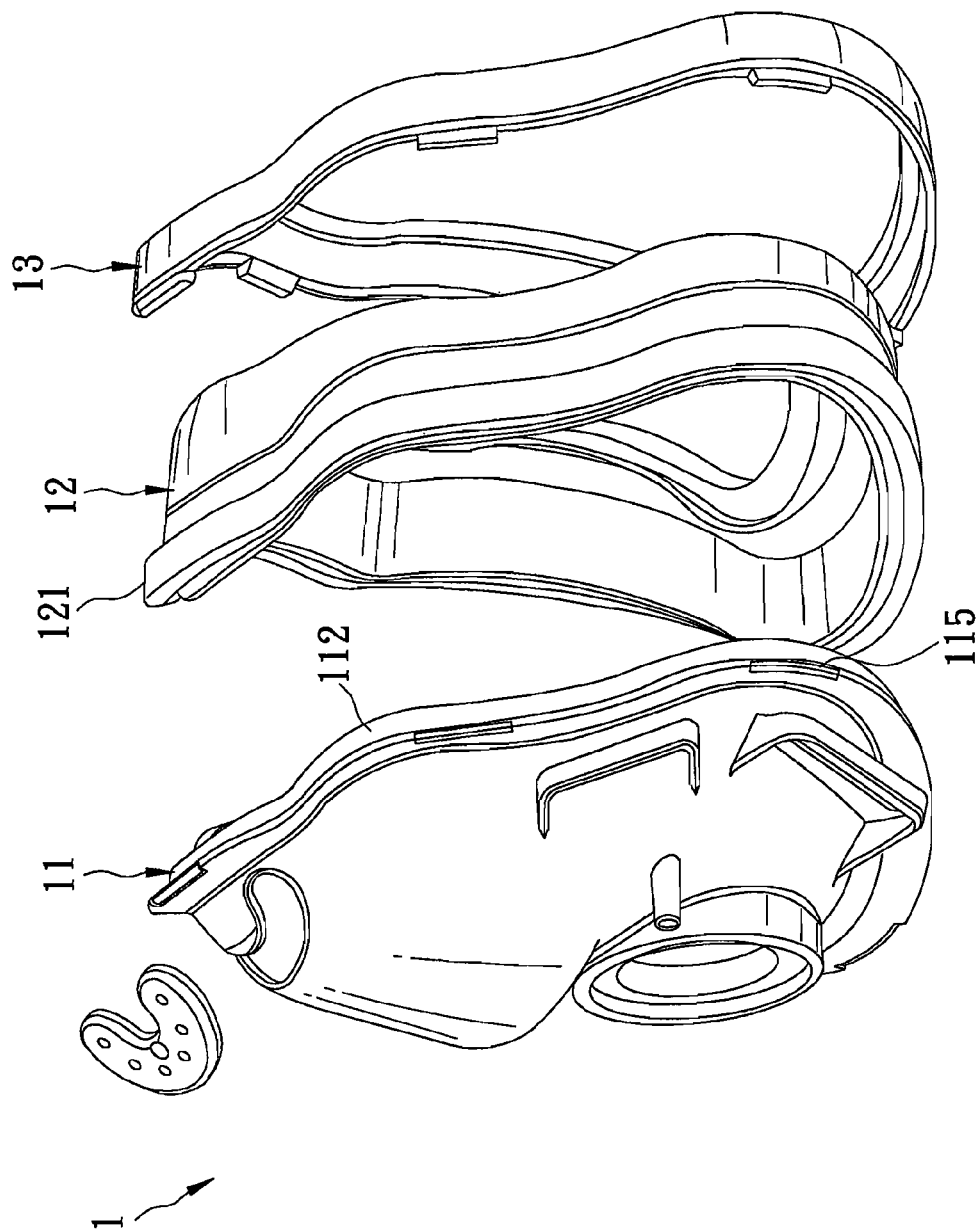
FIG. 1 is an exploded perspective view of a conventional respiratory mask.
Figure 2:
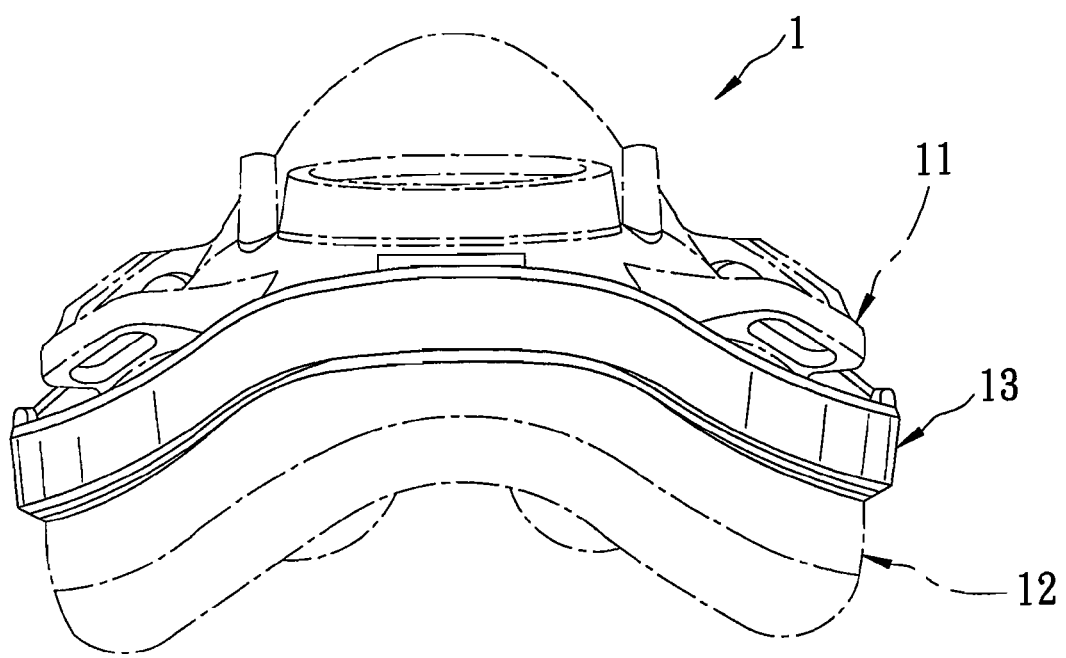
FIG. 2 is a schematic view of the conventional respiratory mask.
Figure 3:
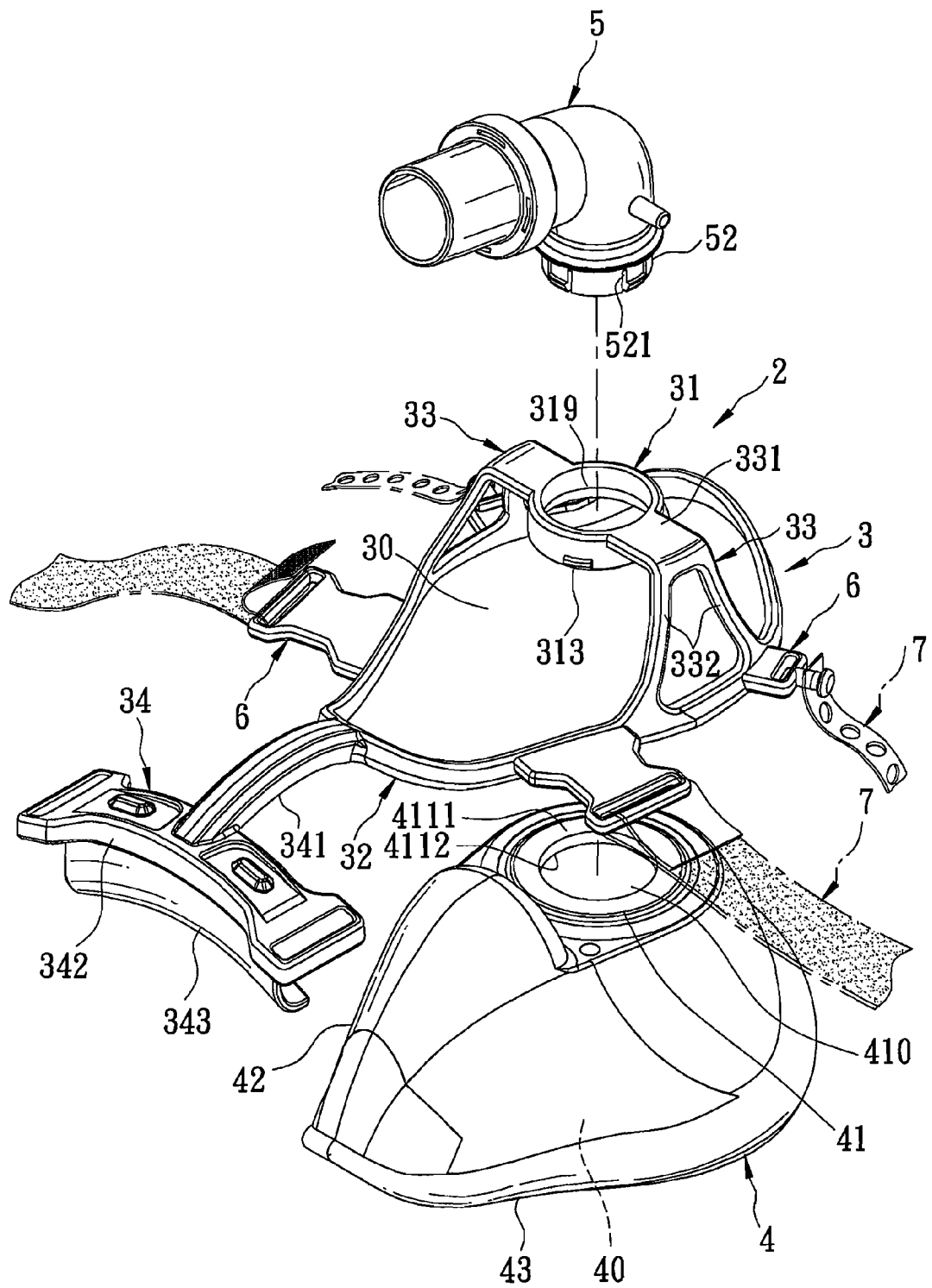
FIG. 3 is an exploded perspective view of the first preferred embodiment of a respiratory mask according to the present invention.
Figure 4:
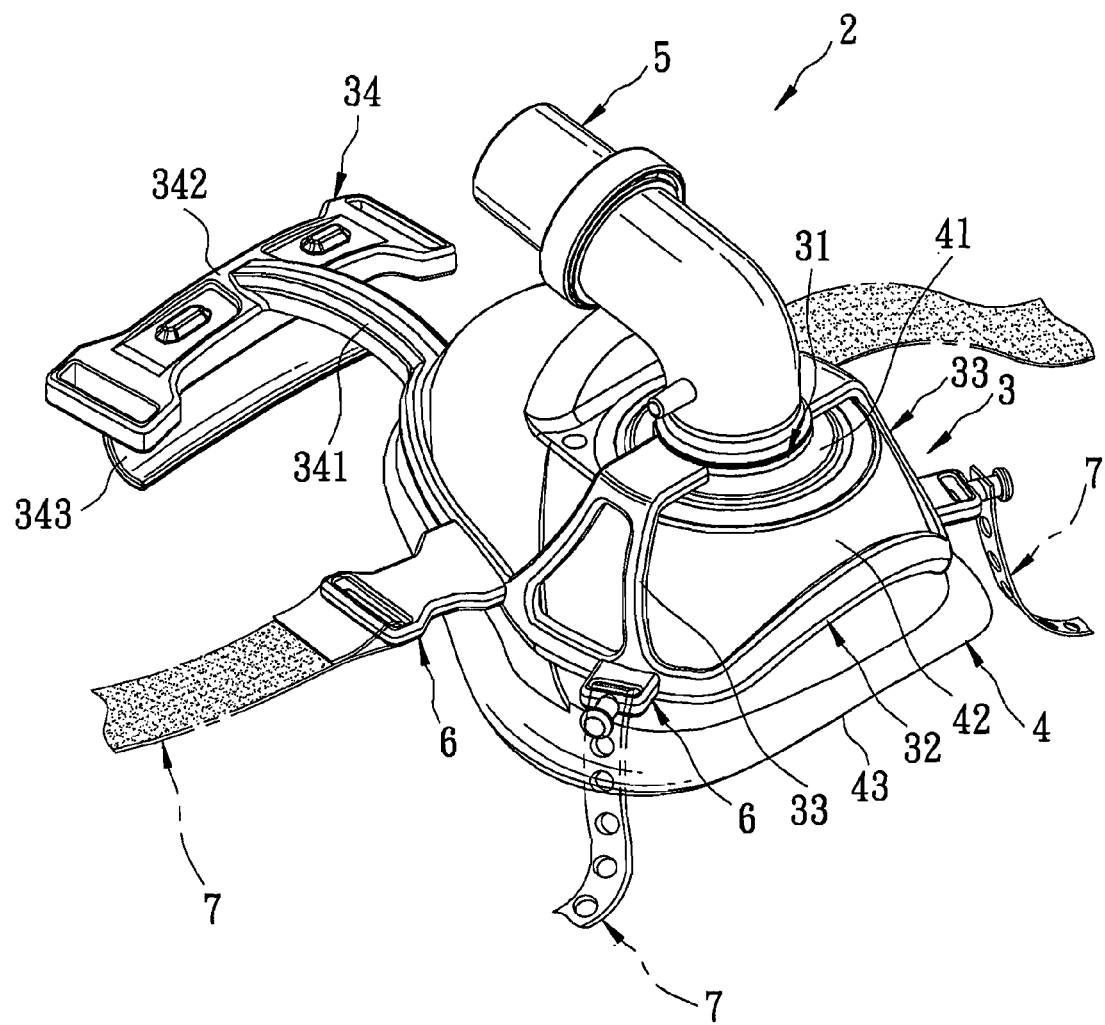
FIG. 4 is an assembled perspective view of the first preferred embodiment.
Figure 5:
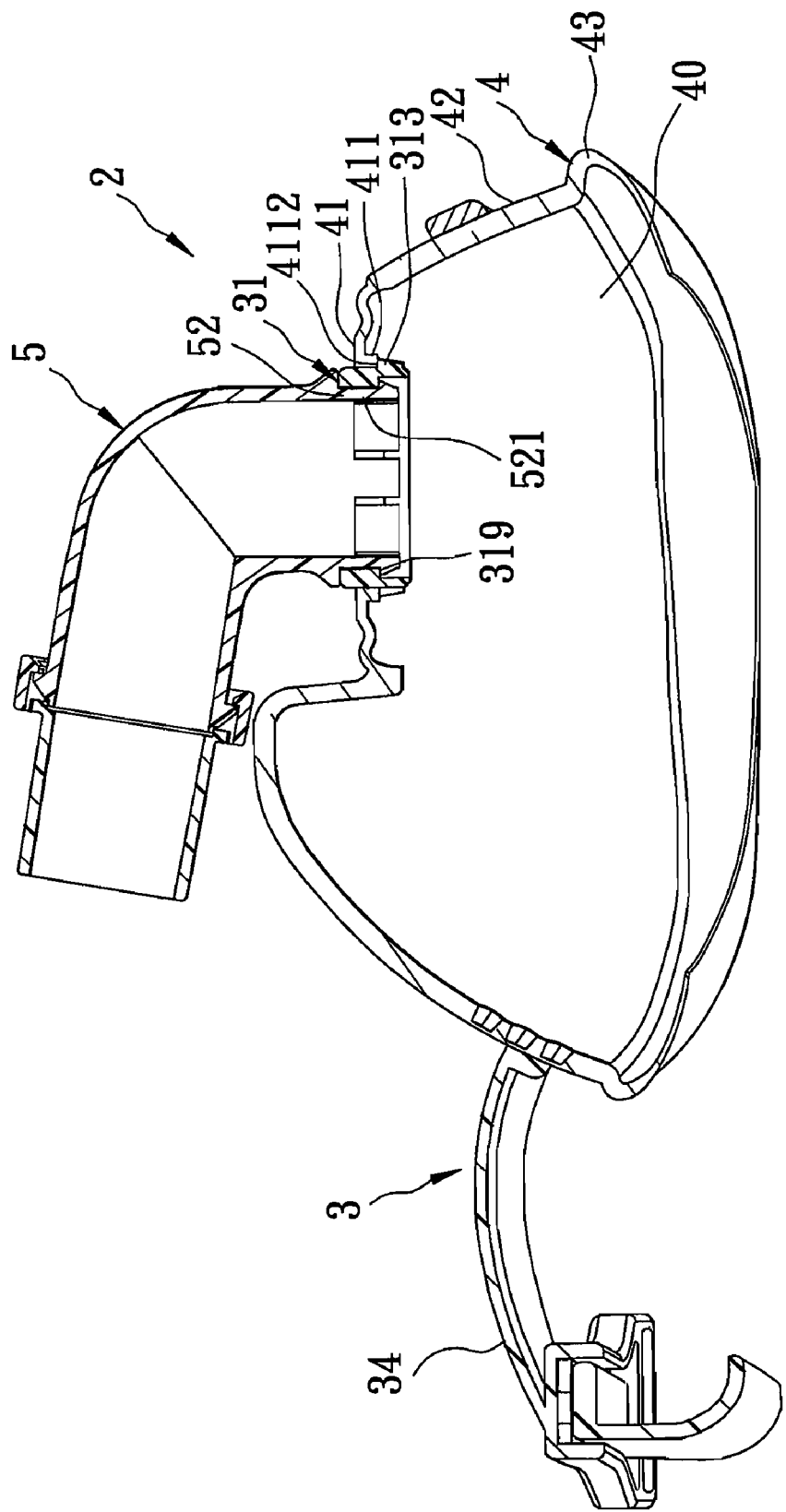
FIG. 5 is a sectional view of the first preferred embodiment.
Figure 6:
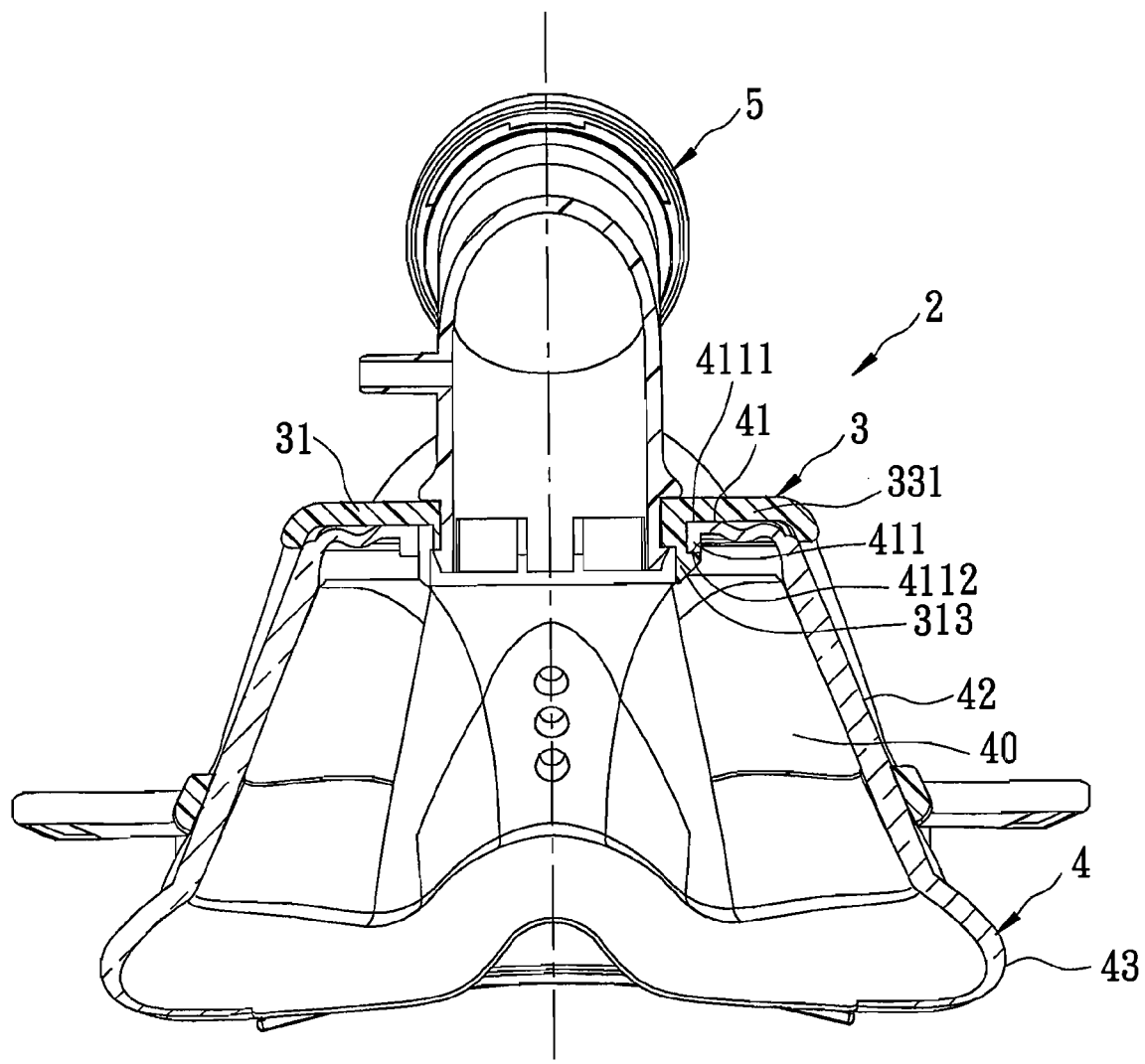
FIG. 6 is another sectional view of the first preferred embodiment.

Before the present invention is described in greater detail with reference to the accompanying preferred embodiments, it should be noted herein that like elements are denoted by the same reference numerals throughout the disclosure.

Referring to FIGS. 3 to 6, the first preferred embodiment of a respiratory mask 2 according to the present invention is shown to include: a rigid mask frame 3 having a ring portion 31, a loop portion 32 spaced apart from the ring portion 31, and rib portions 33 interconnecting the ring portion 31 and the loop portion 32, the rigid mask frame 3 defining a frame space 30; and a single piece of a flexible mask body 4 having a flat central portion 41, a surrounding portion 42 extending outwardly and curvedly from the flat central portion 41, and a peripheral end portion 43 flaring from the surrounding portion 42. The flat central portion 41 of the mask body 4 is formed with an annular flange 411 protruding transversely therefrom and sleeved on the ring portion 31 of the mask frame 3. The peripheral end portion 43 of the mask body 4 is disposed outwardly of the frame space 30. The surrounding portion 42 of the mask body 4 extends into the frame space 30 and is restrained by the rib portions 33 and the loop portion 32 of the mask frame 3.

In this embodiment, the mask body 4 defines an inner space 40. The annular flange 411 of the flat central portion 41 of the mask body 4 extends into the inner space 40, defines a central hole 410 in spatial communication with the inner space 40, and has outer and inner ends 4111, 4112. The ring portion 31 of the mask frame 3 extends through the central hole 410 and into the inner space 40, and is formed with a plurality of protrusions 313. The protrusions 313 abut against the inner end 4112 of the annular flange 411. Each of the rib portions 33 has a first segment 331 radiating outwardly from the ring portion 31 and abutting against the outer end 4111 of the annular flange 411, and a second segment 332 bent from the first segment 331 to connect to the loop portion 32 of the mask frame 3. In this embodiment, the mask body 4 is made from an elastic material, and the peripheral end portion 43 of the mask body 4 is fabricated into different shapes and sizes so as to fit different facial geometries. The first segments 331 of the rib portions 33 of the mask frame 3 and the protrusions 313 of the ring portion 31 of the mask frame 3 cooperatively clamp the flat central portion 41 of the mask body 4 therebetween (see FIG. 6), thereby coupling the mask body 4 to the mask frame 3.

The respiratory mask 2 further includes a T-shaped forehead support 34 extending from the loop portion 32 of the mask frame 3. The forehead support 34 includes a supporting rod 341 having one end connected to a peripheral edge of the loop portion 32 of the mask frame 3, a mounting plate 342 extending transversely from the other end of the supporting rod 341, and a curved pad 343 connected to the mounting plate 342 for contacting the user's forehead.

In this embodiment, the respiratory mask 2 further includes a pipe 5 extending fittingly into the ring portion 31 of the mask frame 3. The ring portion 31 of the mask frame 3 is formed with an annular inner shoulder 319 (see FIG. 5). The pipe 5 has an engaging end portion 52 that is formed with a plurality of resilient hooked tabs 521 that are in snap engagement with the inner shoulder 319.

The respiratory mask 2 further includes a harness unit including a plurality of straps 7 connected to the loop portion 32 of the mask frame 3 through a plurality of lugs 6 formed on the loop portion 32 of the mask frame 3.

The flat central portion 41 of the mask body 4 is annular in shape, and the surrounding portion 42 of the mask body 4 has a size similar to a full face-type mask that covers the facial and nasal areas.

Figure 7:
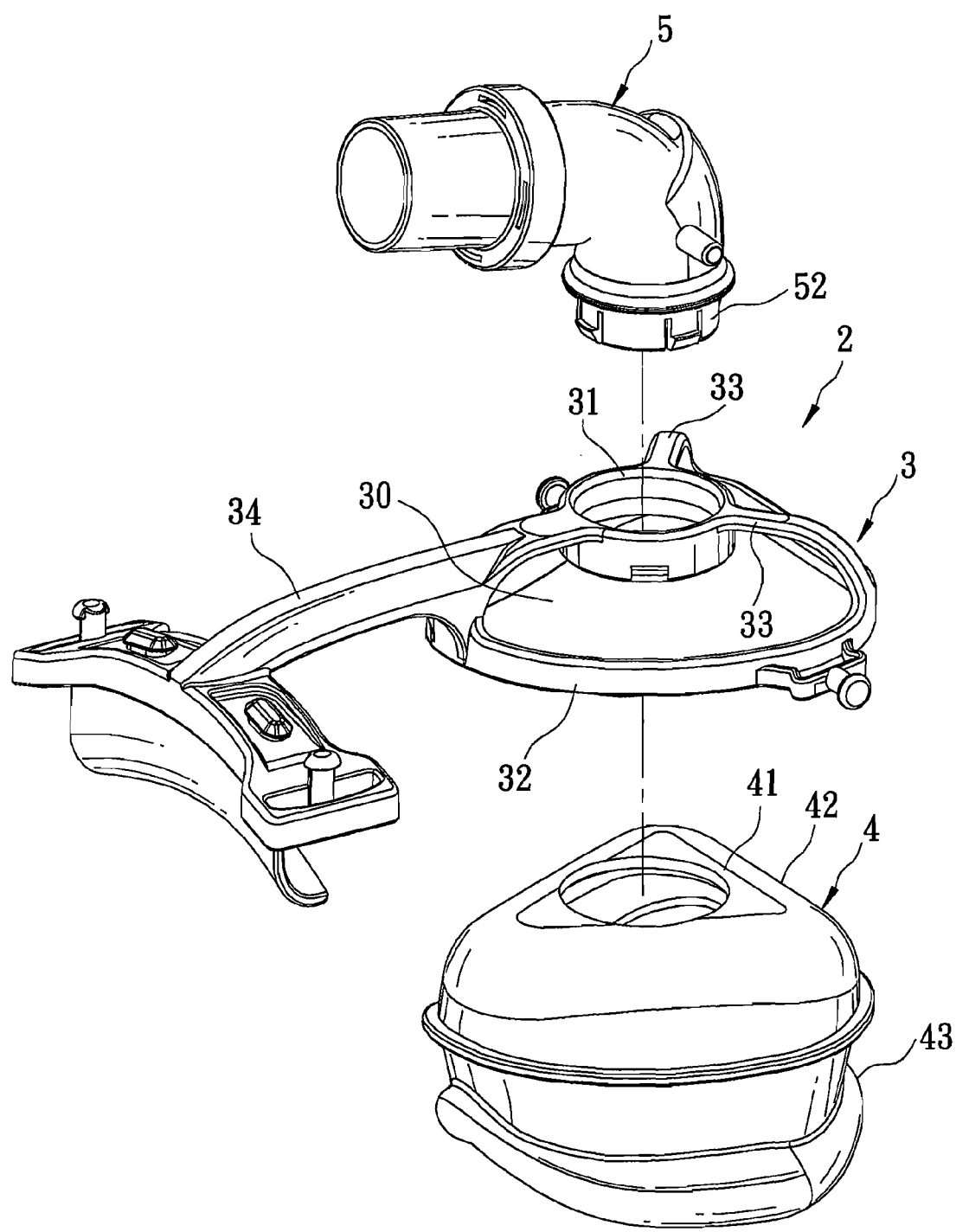
FIG. 7 is an exploded perspective view of the second preferred embodiment of a respiratory mask according to this invention.

FIG. 7 illustrates the second preferred embodiment of the respiratory mask 2 according to this invention. The second preferred embodiment differs from the previous embodiment in that the flat central portion 41 of the mask body 4 is triangular in shape and that the surrounding portion 42 of the mask body 4 has a size similar to a nasal-type mask that covers only the nasal area.

By forming the mask frame 3 with the ring portion 31 and the mask body 4 with the annular flange 411, different sizes of the mask bodies 4 can be used for a single size of the mask frame 3, thereby eliminating the aforesaid drawback associated with the prior art.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A respiratory mask comprising:
   a rigid mask frame having a ring portion, a loop portion spaced apart from said ring portion, and rib portions interconnecting said ring portion and said loop portion, said rigid mask frame defining a frame space; and
   a single piece of a flexible mask body having a flat central portion, a surrounding portion extending outwardly and curvedly from said flat central portion, and a peripheral end portion flaring from said surrounding portion, said flat central portion of said mask body being formed with an annular flange protruding therefrom and sleeved on said ring portion of said mask frame, said peripheral end portion being disposed outwardly of said frame space, said surrounding portion extending into said frame space and being restrained by said rib portions and said loop portion of said mask frame.

2. The respiratory mask as claimed in claim 1, wherein said mask body defines an inner space, said annular flange of said flat central portion of said mask body extending into said inner space, defining a central hole, and having inner and outer ends, said ring portion of said mask frame extending through said central hole and into said inner space and being formed with a plurality of protrusions, said protrusions abutting against said inner end of said annular flange, each of said rib portions having a first segment radiating outwardly from said ring portion and abutting against said outer end of said annular flange, and a second segment bent from said first segment to connect to said loop portion of said mask frame.

3. The respiratory mask as claimed in claim 1, wherein said mask body is made from an elastic material.

4. The respiratory mask as claimed in claim 1, further comprising a T-shaped forehead support extending from said loop portion of said mask frame.

5. The respiratory mask as claimed in claim 1, further comprising a pipe extending fittingly into said ring portion of said mask frame.

6. The respiratory mask as claimed in claim 5, wherein said ring portion of said mask frame is formed with an inner shoulder, said pipe having an engaging end portion that is formed with a plurality of resilient hooked tabs that are in snap engagement with said inner shoulder.

7. The respiratory mask as claimed in claim 1, further comprising a harness unit including a plurality of straps connected to said loop portion of said mask frame.

\* \* \* \* \*